(12) United States Patent
Lin et al.

(10) Patent No.: US 7,064,562 B2
(45) Date of Patent: Jun. 20, 2006

(54) TEMPERATURE COMPENSATION METHOD FOR SOOT SENSOR

(75) Inventors: Yingjie Lin, El Paso, TX (US); Nicte Salvador, Chihauhau (MX)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/909,272

(22) Filed: Jul. 30, 2004

(65) Prior Publication Data

US 2005/0017738 A1    Jan. 27, 2005

Related U.S. Application Data

(63) Continuation-in-part of application No. 10/310,126, filed on Dec. 4, 2002, now Pat. No. 6,867,603.

(51) Int. Cl.
*G01R 27/26* (2006.01)

(52) U.S. Cl. .................. 324/698; 324/708; 324/655

(58) Field of Classification Search .............. 324/698, 324/708, 709, 601, 655
See application file for complete search history.

(56) References Cited

U.S. PATENT DOCUMENTS

| | | | | |
|---|---|---|---|---|
| 2,720,624 A | * | 10/1955 | Burton et al. ............ | 324/668 |
| 3,746,974 A | * | 7/1973 | Stoakes et al. .......... | 324/686 |
| 4,112,744 A | | 9/1978 | Tassano .................. | 73/61.61 |
| 4,281,533 A | | 8/1981 | Eesley et al. ........... | 73/61.76 |
| 4,345,202 A | | 8/1982 | Nagy et al. .............. | 324/642 |
| 4,503,384 A | | 3/1985 | Nagy et al. .............. | 324/690 |
| 4,646,070 A | | 2/1987 | Yasuhara et al. ........ | 340/603 |
| 4,733,556 A | | 3/1988 | Meitzler et al. ......... | 73/53.05 |
| 4,926,120 A | | 5/1990 | Veronesi et al. ........ | 324/204 |
| 5,225,783 A | * | 7/1993 | Suzuki et al. ........... | 324/655 |
| 5,270,663 A | * | 12/1993 | Sano et al. ............... | 324/676 |
| 5,604,441 A | | 2/1997 | Freese, V et al. ....... | 324/663 |
| 5,656,767 A | | 8/1997 | Garvey, III et al. ..... | 73/61.44 |
| 5,824,889 A | | 10/1998 | Park et al. ................ | 73/116 |
| 6,508,100 B1 | | 1/2003 | Berndorfer .............. | 73/1.02 |
| 6,509,749 B1 | | 1/2003 | Buelna et al. ........... | 324/698 |
| 6,535,001 B1 | | 3/2003 | Wang ..................... | 324/698 |
| 6,557,396 B1 | | 5/2003 | Ismail et al. ............ | 73/53.05 |

(Continued)

FOREIGN PATENT DOCUMENTS

WO    WO 9846985 A1  *  10/1998

OTHER PUBLICATIONS

"Standard Test Method for Evaluation of Diesel Engine Oils in T-8 Diesel Engine," ASTM, Designation: D 5967-99, An American National Standard, Aug. 1999.

(Continued)

*Primary Examiner*—Anjan Deb
(74) *Attorney, Agent, or Firm*—Jimmy L. Funke

(57) ABSTRACT

Certain characteristics of Diesel engine lubrication oil are determined. A sensor formed as a capacitor is immersed in the oil. An inductor is in series with the sensor, and a high frequency voltage with a varying frequency is applied to the resonance circuit formed by the inductor and capacitor. Resonance is sensed, and the resonant frequency and/or the resonant current are used to determine the soot content and/or the dielectric constant of the oil. The electronics temperature can be used to compensate for temperature variations in the resonant frequency and the electronics temperature and the oil temperature can be used to compensate for temperature variations in the resonant current. The compensated values are preferably used in the determination of soot content and the dielectric constant.

25 Claims, 12 Drawing Sheets

U.S. PATENT DOCUMENTS

| | | | |
|---|---|---|---|
| 6,564,126 B1 | 5/2003 | Lin et al. | 701/30 |
| 6,867,603 B1* | 3/2005 | Nicholson et al. | 324/698 |
| 2004/0036487 A1 | 2/2004 | Heremans et al. | 324/698 |
| 2004/0108859 A1 | 6/2004 | Nicholson et al. | 324/633 |
| 2004/0239344 A1* | 12/2004 | Hu | 324/698 |

OTHER PUBLICATIONS

Ian White et al, "Effect of Bulk Electrical Conductivity on TDR Measurement of Water Content in Porous Media," Symposium and Workshop on Time Domain Reflectometry in Environmental, Infrastructure, and Mining Applications held at Northwestern University, Evanston, Illinois, Sep. 17-19, 1994 (Washington DC: US Bureau of Mines, 1994) pp. 294-308.

George S. Saloka et al, "A capacitive oil deterioration sensor," Electronic Material and Devices Dept., Ford Motor Co., SAE No. 910497.

Eckard Irion et al, "Oil-Quality Prediction and Oil-Level Detection with the TEMIC QLT-Sensor Leads to Variable Maintenance Intervals," SAE No. 970847, 1997.

Peter E.M. Frere et al, "An On-Line Oil Viscosity Sensor," SAE No. 970848, 1997.

* cited by examiner

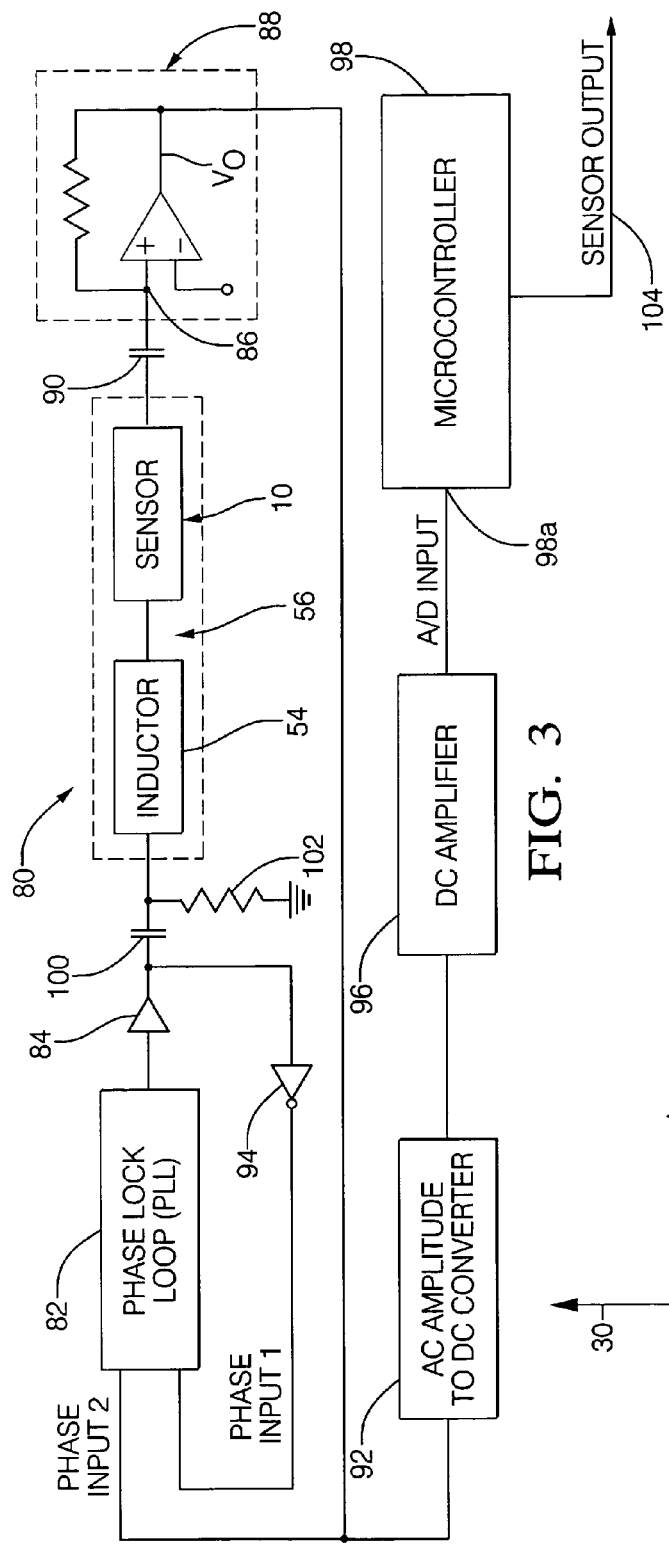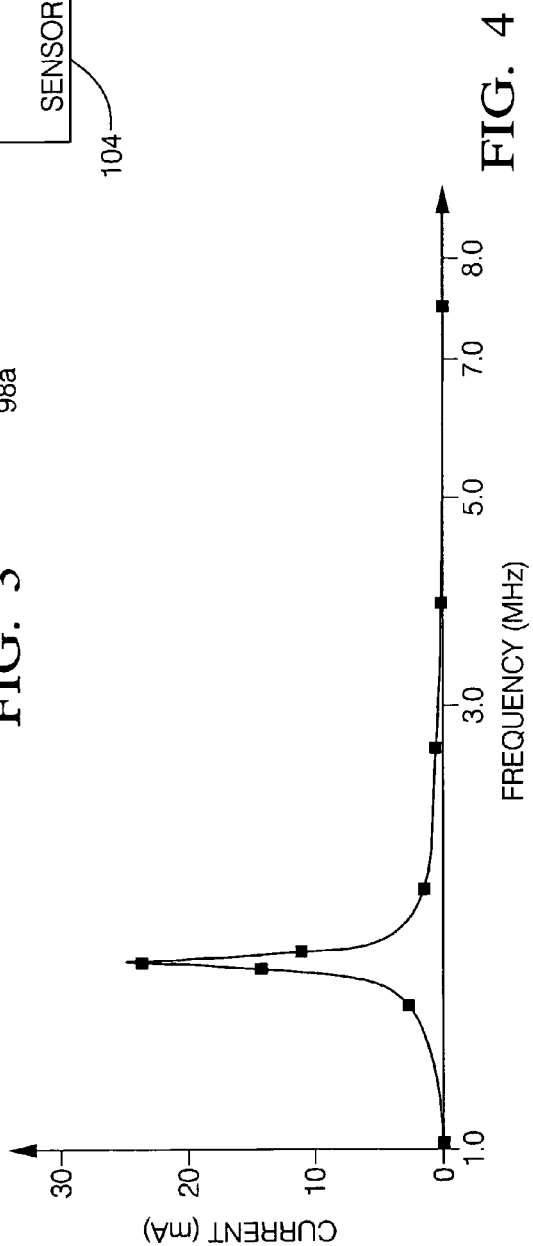
FIG. 3
FIG. 4

TEMPERATURE COMPENSATION METHOD FOR SOOT SENSOR

RELATED APPLICATIONS

This application is a continuation-in-part of U.S. application Ser. No. 10/310,126, which was filed on Dec. 04, 2002, now U.S. Pat. No. 6,867,603 issued Mar. 15, 2005, and is incorporated herein in its entirety by reference.

TECHNICAL FIELD

The present invention relates generally to Diesel engine oil contaminant sensors, and more particularly to a method for determining soot contamination of Diesel engine lubrication oil by measuring the AC conductivity thereof at high frequency.

BACKGROUND OF THE INVENTION

When engine oil becomes contaminated with the by-products of combustion, its value as a lubricant is greatly diminished. The main contaminate in engine oil during normal combustion is carbon. Diesel engines produce large amounts of carbon referred to as soot during combustion, and the measurement of the percentage of soot in the diesel oil gives an indication of when the oil should be changed.

Measurement attempts at DC and low frequency AC (i.e., below about one kHz) fail because the change in conductivity is very small for large changes in the percentages of soot. At high frequencies (i.e., in the MHz range) the AC conductivity changes due to the soot are measurable even at levels of less than one percent soot. The problem with the high frequency AC conductivity measurement is that the sensor, which defines a measurement volume, is a capacitor. Since the sensor has a capacitance associated with its physical shape, there is also a capacitive reactance associated with the sensor. The problem arises because the oil capacitance conductivity is high at these high frequencies, and the conductivity contribution of the soot in oil (small conductive particles mixed with oil), which can be theoretically modeled as a capacitance-resistance network, is relatively low. There are methods that are used in a laboratory that can make the measurement, but the equipment is expensive and the setup must be nearly ideal (very short leads). The use of a network analyzer or vector voltmeter is cost prohibitive. An RF bridge measurement could be used if the resistance and capacitive reactance were near the same values. These drawbacks make such measurements very difficult in the real-world environment of an operating engine.

Accordingly, what is needed in the art is a method, applicable to real-world engine operation environments, for determining contamination of Diesel engine lubrication oil by measuring the AC conductivity thereof at high frequency.

SUMMARY OF THE INVENTION

The invention proposes a method for determining contamination of Diesel engine lubrication oil by measuring the AC conductivity thereof at high frequency while preferably compensating for temperature variations in the operating environment of the sensor apparatus during actual operations.

The method for determining certain characteristics of Diesel engine lubrication oil comprises the steps of immersing a capacitor in the oil such that the oil provides a dielectric between the plates thereof, connecting an inductor in series with the capacitor, wherein the capacitor and the inductor collectively provide a resonance circuit, varying a frequency of a high frequency voltage applied to the resonance circuit, sensing when the resonance circuit is at resonance and using the resonant frequency and/or resonant current to determine the soot content and/or the dielectric constant of the oil.

Preferably, measurements are taken of the temperature of the electronics (i.e., the inductor) and the oil. The inductor temperature can be used to compensate for temperature variations in the resonant frequency, and the electronics temperature and the oil temperature can be used to compensate for temperature variations in the resonant current. The compensated values are preferably used in the determination of soot content and the dielectric constant.

Additional features of the invention are described hereinafter, and other applications of the present invention will become apparent to those skilled in the art when the following description of the best mode contemplated for practicing the invention is read in conjunction with the accompanying drawings.

BRIEF DESCRIPTION OF THE DRAWING

The description herein makes reference to the accompanying drawings wherein like reference numerals refer to like parts throughout the several views, and wherein:

FIG. 3 is a second example of an electrical circuit to measure resistance of Diesel engine lubrication oil at high frequencies;

FIG. 4 shows a computer simulation that graphs the current increase at resonance of an electrical circuit of FIG. 2 or 3;

DESCRIPTION OF THE PREFERRED EMBODIMENT

Figure 1A:
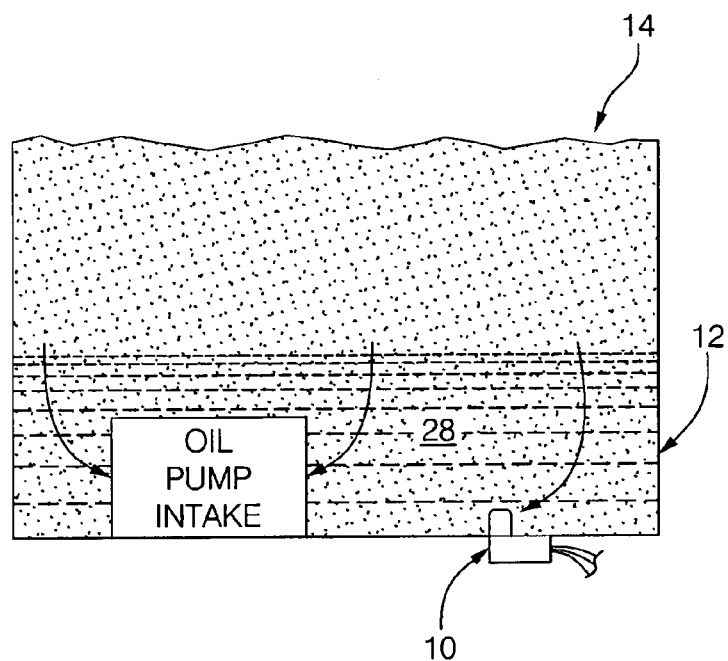
FIG. 1A depicts the engine placement of an oil sensor for resistance measurements according to the present invention.
Figure 1B:
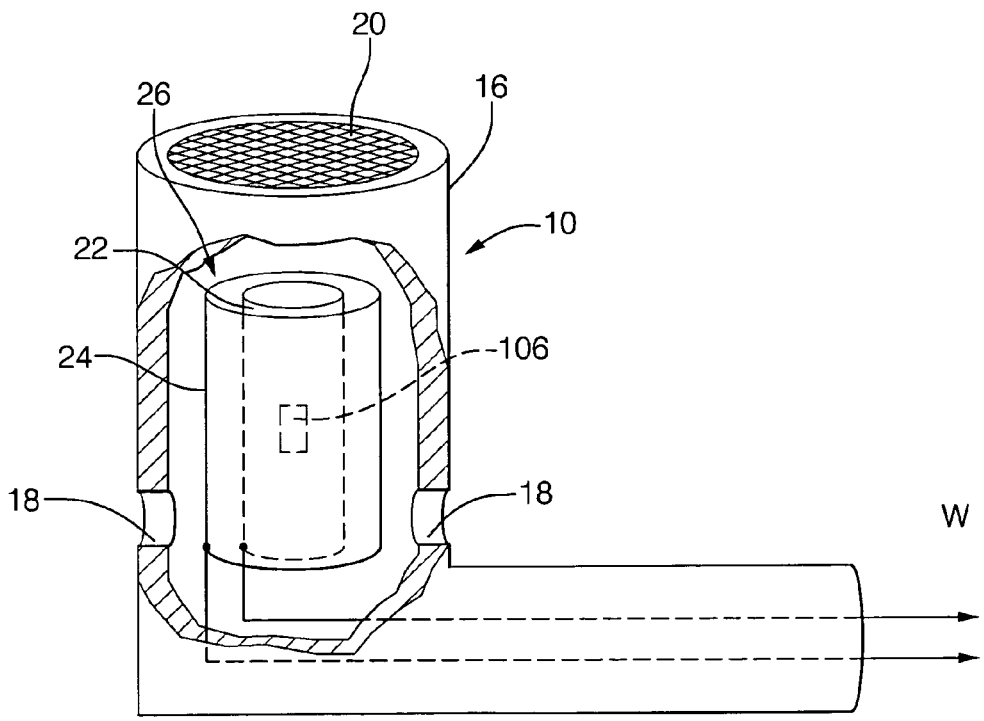
FIG. 1B depicts a detail view of the oil sensor of FIG. 1.

Referring now to the drawing, FIG. 1A depicts an environment of placement and operation of a Diesel engine lubrication oil condition sensor 10. The sensor 10 is located at the bottom of an oil pan 12 of a Diesel engine 14. As shown at FIG. 1B, the oil sensor 10 has a grounded cylindrical shell, or shielding tube, 16 having apertures 18 and an open top end 20. Inside the shell 16 is a pair of concentrically arranged and mutually separated cylindrical capacitor plates 22, 24 that collectively form a capacitor 26, each of which being connected to a respective portion of wiring W. A temperature sensor 106 located within the plate 22 will be discussed in detail hereinafter.

In operation of the sensor 10, which construction is known in the prior art, oil 28 in the oil pan 12 sloshes, causing the oil to flowably fill the space separating the plates 22, 24. As a result, the capacitance C and the resistance R (see FIG. 2) of the space between the plates 22, 24 changes over time as the condition of the oil changes with hours of operation of the Diesel engine 14.

Figure 2:
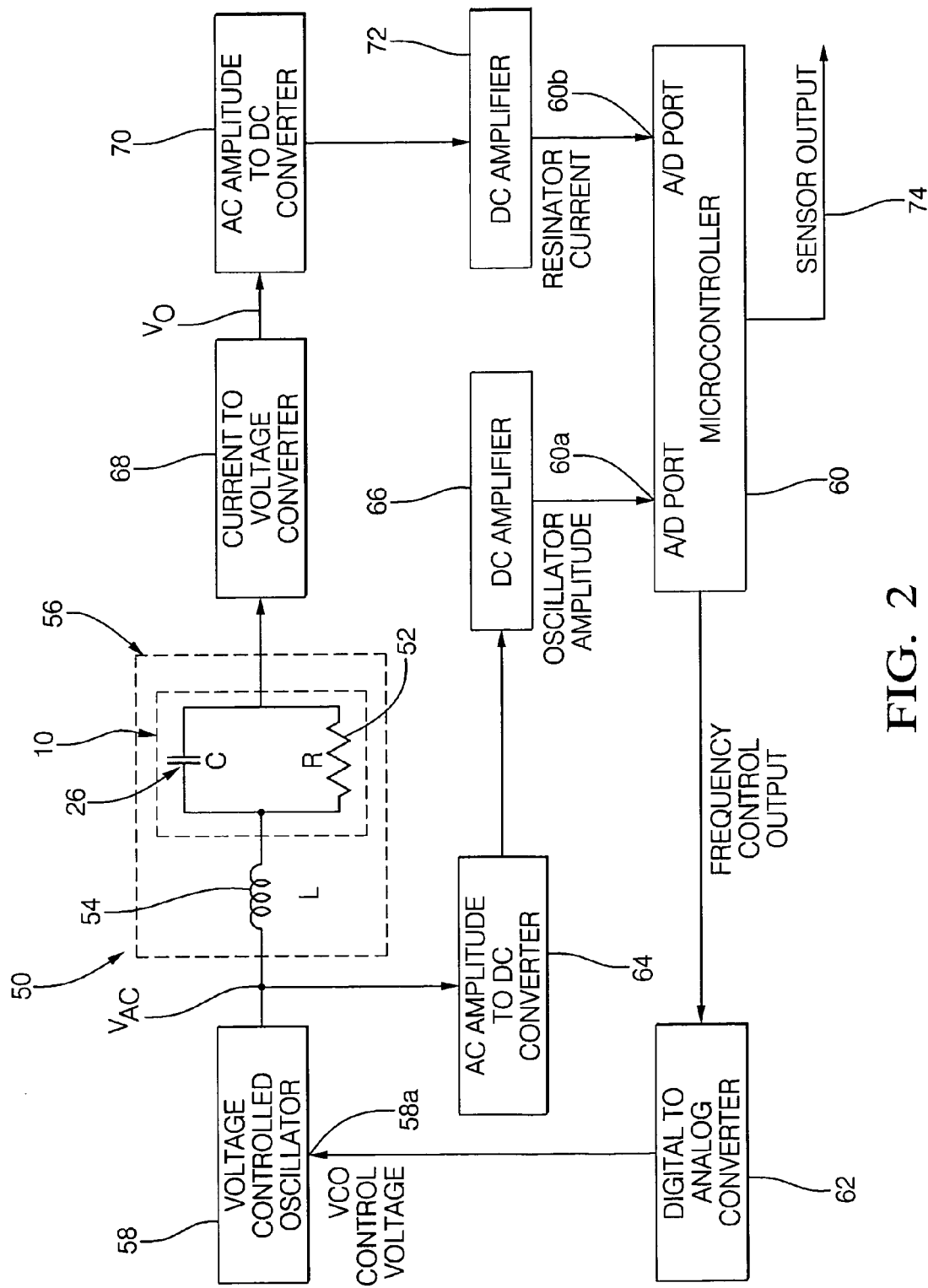
FIG. 2 is a first example of an electrical circuit to measure resistance of Diesel engine lubrication oil at high frequencies.

FIG. 2 is a first example of an electrical circuit 50 to measure resistance of Diesel engine lubrication oil at high frequencies utilizing a series resonant LC circuit. The soot particles (small conductive carbon particles) mixed with engine oil between electrodes form a capacitance-resistance network. This capacitance-resistance network can be replaced by a lumped capacitor and lumped resistor equivalent circuit. The sensor 10 is modeled as the aforesaid capacitor 26 having a capacitance C with a resistor 52 have a resistance R in parallel therewith, wherein C represents the capacitance of the physical configuration of the metal plates (22, 24 of FIG. 1B) of the sensor 10 filled with the oil. An inductor 54 having an inductance L is chosen in accordance with the dimensions of the sensor 10 to provide an LC series resonance circuit 56 having resonance over a predetermined frequency range, for example between two and four MHz.

The Diesel engine lubrication oil 28 provides a dielectric constant for the capacitor 26. As carbon contaminates (soot) build up in the oil, the capacitor 26 behaves like a capacitance-resistance network. The high frequency AC conductivity of the diesel engine oil at room temperature in the two MHz frequency range is around 1.5 μσ ($10^{-6}\Omega^{31\ 1}m^{-1}$) for fresh oil and above four (4)μσ for eight percent soot content in oil.

It is well known in the art that at resonance the phase vectors of a capacitive reactance and an inductive reactance cancel, leaving only a resistive value. Since the range of relative dielectric constants for Diesel engine oil is known to be between two and four, the range of capacitance C is also known, as is the frequency range over which resonance will occur. Thus, a voltage controlled oscillator (VCO) 58 of the electrical circuit 50 is preselected to cover the predetermined range of frequencies over which resonance of the resonance circuit 56 will occur due to changes of the dielectric constant of the capacitor 26. At resonance of an LCR network, because the capacitance reactance and the inductance reactance cancel each other, the network shows pure resistance behavior. The resonance loop current is proportional to the LCR network conductivity.

In FIG. 2, a microcontroller 60 outputs a stream of bit patterns to a digital-to-analog converter (D/A converter) 62 that outputs a changing, ramp-like, analog voltage. The analog voltage ramp is connected to a control input 58a of the VCO 58. The output of the VCO 58 is a sweep of frequencies over the range of interest for providing resonance. The output of the VCO 58 is connected to the resonant circuit 56 and to an AC amplitude to DC converter 64. The DC output of the AC amplitude to DC converter 64 is amplified by a DC amplifier 66 and connected to an A/D input port 60a of the microcontroller 60, which monitors the AC voltage level $V_{AC}$ being fed into the resonant circuit 56. The resonance circuit 56 consists of the aforementioned LC series resonant circuit 56, comprising the inductor 54, having a fixed inductance L, and the sensor 10, wherein the sensor includes the capacitor 26 having a changing capacitance C and the resistor 52 having a changing resistance R in parallel therewith, the changing values of capacitance and resistance being related to the condition of the oil.

The output of the resonant circuit 56 is connected to a current-to-voltage converter 68 that converts the current flowing in the resonant circuit 56, i.e., the loop current, to a proportional AC voltage output $V_0$. The output of the current-to-voltage converter 68 is connected to an AC amplitude to DC converter 70, whose output is amplified by DC amplifier 72 and connected to an A/D input port 60b of the microcontroller 60 monitoring the AC voltage level $V_0$. As the microcontroller 60 varies the input control voltage to the VCO 58, the VCO output frequency is swept into the resonance circuit 56. The AC output voltage $V_0$ is monitored by the microprocessor 60 at the A/D port 60b until a maximum voltage is detected. At this maximum voltage, the VCO output $V_{AC}$ is at the resonant frequency of resonant circuit 56, and the loop current is at a maximum. In this regard, FIG. 4 shows a computer simulation plot 76 of how the loop current increases at resonance.

The microcontroller 60 stores the maximum (peak) current and the voltage amplitude and then calculates the relative resistance of the oil. This loop current at resonance is called hereinafter the resonant current. The microcontroller 60 then outputs a signal 74 in a format that is required by external electronics. In this regard, the microcontroller 60 has incorporated within it all parameters, constants, algorithms, and programs to effect the operation of the circuit 50 and the present invention utilizing techniques well known in the art.

FIG. 3 is a second example of an electrical circuit 80, which is the most preferred method of the present invention to measure resistance of Diesel engine lubrication oil at high frequencies, wherein a phase locked loop (PLL) 82 integrated circuit is used in conjunction with the resonance circuit 56 previously described.

A voltage-controlled oscillator (VCO) incorporated within the PLL 82 is set to free-run at a frequency that is in the range of frequencies expected due to the change of dielectric constant of the oil within the sensor 10, as previously described in FIG. 2. The VCO output of PLL 82 is buffered by a buffer 84 to provide the required drive current to the resonance circuit 56. The current flowing in the resonance circuit 56 is connected to the virtual ground input 86 of a current to voltage converter 88 through a DC blocking capacitor 90. The voltage output $V'_0$ of the current to voltage converter 88 is connected to one of the phase input terminals (Phase Input 2, or the current phase input) of the PLL 82 and to an AC amplitude to DC converter 92. The output of the buffer 84 is inverted by a phase inverter 94 to account for the phase inversion in output $V'_0$ by the current to voltage converter 88, and is connected to another of the phase input terminals (Phase Input 1, or the voltage phase input) of the PLL 82.

The phase of the voltage output $V'_0$ of the current to voltage converter 88 at Phase Input 2 of PLL 82 will lead or lag the VCO output of the PLL 82 above or below resonance of the resonant circuit 56, and will only be in phase with the voltage at Phase Input 1 at resonance, due to the fact that at resonance, the resonance circuit 56 is purely resistive. In this regard, at resonance, the voltage across the resonance circuit 56, represented by the voltage at Phase Input 1 of the PLL 82, is in phase with the current through the resonance circuit represented by the voltage $V'_0$ at Phase Input 2 taking into account the phase shift produced by the current-to-voltage converter 88 and compensated for by the phase inverter 94.

When phase information is presented to the PLL 82 through input signals at Phase Input 1 and at Phase Input 2, an internal error signal is generated within the PLL 82 if an out-of-phase condition exists. This error signal is filtered and connected to an internal VCO control pin, which changes the VCO frequency until the input signals at Phase Input 1 and at Phase Input 2 are in phase, at which time the PLL 82 locks, the VCO frequency does not change, and resonance is present. Under this resonating condition, the VCO control input voltage is proportional to the resonating frequency.

The output of the AC amplitude to DC converter 92 is fed to a DC amplifier 96, the output of which is connected to an A/D input 98a of a microcontroller 98. A capacitor 100 serves as a DC blocking capacitor and passes the high frequencies from the VCO output of the PLL 82 and the buffer 84 to the resonance circuit 56. A resistance 102 establishes a ground reference for the high frequency AC voltage passed by the capacitor 100. The VCO output of the PLL 82 is a constant amplitude square wave, thereby providing a constant voltage to the resonant circuit 56.

A convenient voltage amplitude can be selected for calculation by the microcontroller 98 along with the current of the resonant circuit 56 at resonance, represented by the voltage at the A/D input 98a of the microcontroller 98. The microcontroller 98 then calculates the high frequency AC conductivity introduced by the soot in the oil, and thereupon outputs a signal 104 that is related to the percentage of soot in the Diesel engine oil in a format required by, for example, an "Engine Management System." With fresh oil, the AC conductivity is relatively low (low resonate loop current), and with the soot contamination in the oil, the AC conductivity increases. Also, with the soot concentration increasing in the oil, the contaminated oil dielectric constant increases (this causes the resonating frequency to decrease).

The microcontroller 98 has incorporated within it all parameters, constants, algorithms, and programs to effect the operation of the circuit 80 and the present invention by techniques well known in the art.

In the invention described thus far, both the resonance frequency and the resonant current information are used to determine the percentage of soot. Under constant conditions, for instance at room temperature or inside an oven that has been set to a constant temperature, the circuits 50, 80 work well, and sensor output is repeatable. However, testing on a vehicle results in sensor output that is not repeatable. The root cause of the problem is the temperature. Calibration of the sensor 10 was performed inside an oven at predefined oil temperature, say 60 or 70 degrees C. Under this calibration condition, the temperature of the electronics was also close to the oil temperature. After installation of the sensor 10 on a vehicle, the oil temperature was measured. The sensor 10 started soot measurement at the calibration oil temperature, but the electronics board temperature was found to vary between the oil temperature and the ambient temperature. The PCB temperature, most influenced by the inductor temperature, impacts both resonance frequency and the loop current. The addition of temperature compensation can reduce the ambient temperature impact and also give the sensor the capability to measure the soot over a relatively large oil temperature range instead of only at calibration temperature point(s).

Figure 5:
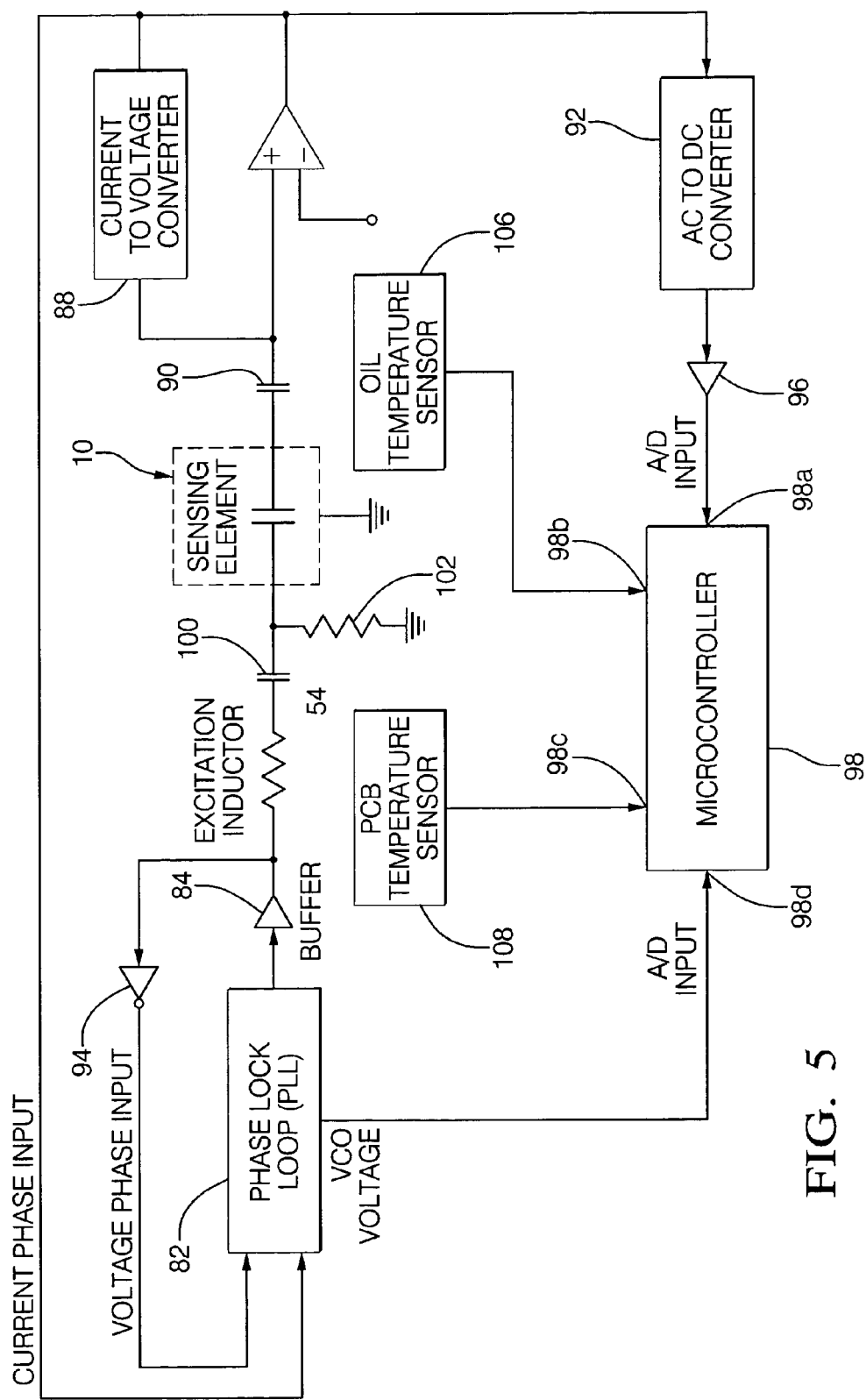
FIG. 5 is a modified schematic of the electrical circuit of FIG. 3 including the oil temperature sensor and the PCB temperature sensor.

In order to perform this temperature compensation, one temperature sensor 106 measures the oil temperature, and an additional temperature sensor 108 measures the temperature of the electronics mounted on the printed circuit board (not shown). Referring back to FIG. 1B, the temperature sensor 106 is a silicon temperature sensor and is located inside the receiver tube, plate 22, such that the temperature sensor 106 is in contact with the engine oil 28. The temperature sensor 106 is shown schematically in FIG. 5, which is a slightly modified schematic of the circuit 80 of FIG. 3. As shown in FIG. 5, the oil temperature sensor 106 supplies a temperature-related signal to an input 98b the microcontroller 98.

Also shown in FIG. 5 is the printed circuit board (PCB) temperature sensor 108, which supplies a temperature-related signal to an input 98c of the microcontroller 98. The PCB temperature sensor 108 is preferably placed near the excitation inductor 54 because the inductance of the inductor 54 provides the largest contribution to the total temperature variation. Finally, FIG. 5 shows a variation of the invention whereby the microcontroller 98 can sample the VC voltage of the PLL IC 82 through an A/D input 98d.

Testing shows that the resonating frequency is a function of oil quality and PCB temperature and is independent of oil temperature. More specifically, for a given oil the resonating frequency has linear relationship with the PCB temperature. Testing further shows that the loop current is a function of both oil and PCB temperatures. Specifically, within the oil temperature range from room temperature (about 30 degrees C.) up to about 70 to 80 degrees C., the loop current has an approximately linear relationship with the oil temperature and with the temperature difference between the oil and the PCB temperatures. Given these test results, compensation for temperature variations is possible.

In the sensor 10, this compensation can be done by converting the real measured frequency and loop current to their equivalent values at a temperature, such as a room temperature of 30° C. In this way, only linear equations can be used to do the oil/PCB temperature compensations. The frequency temperature compensation is given by:

$$f_c = m_f(T_{ref} - T_{pcb}) + f_m; \text{ where}$$

$f_c$ is the compensated frequency;

$f_m$ is the measured frequency;

$m_f$ is the frequency slope with PCB temperature (a parameter determined by calibration);

$T_{ref}$ is the reference temperature (i.e., a calibration temperature such as "room" temperature); and
$T_{pcb}$ is the measured PCB temperature.

The temperature-compensated loop current value is given by:

$$V_{lpf} = \overline{M}_{lpf}(T_{ref} - T_{oil}) + \hat{V}_{lpf}; \text{ and}$$

$$\overline{M}_{lpf} = \alpha(T_{oil} - T_{pcb}) + M_{lpf}; \text{ where}$$

$V_{lpf}$ is the compensated loop current value;
$\hat{V}_{lpf}$ is the measured loop current value;
$\overline{M}_{lpf}$ is the compensated slope of loop current with oil temperature;
$M_{lpf}$ is the slope of loop current with oil temperature (a parameter determined by calibration);
$T_{ref}$ is the reference temperature;
$T_{oil}$ is the oil temperature;
$T_{pcb}$ is the PCB temperature; and
α is an adjust factor.

Preferably, the slope of loop current with oil temperature is calibrated under conditions where $T_{oil}$ is much greater than $T_{pcb}$.

Figure 6:
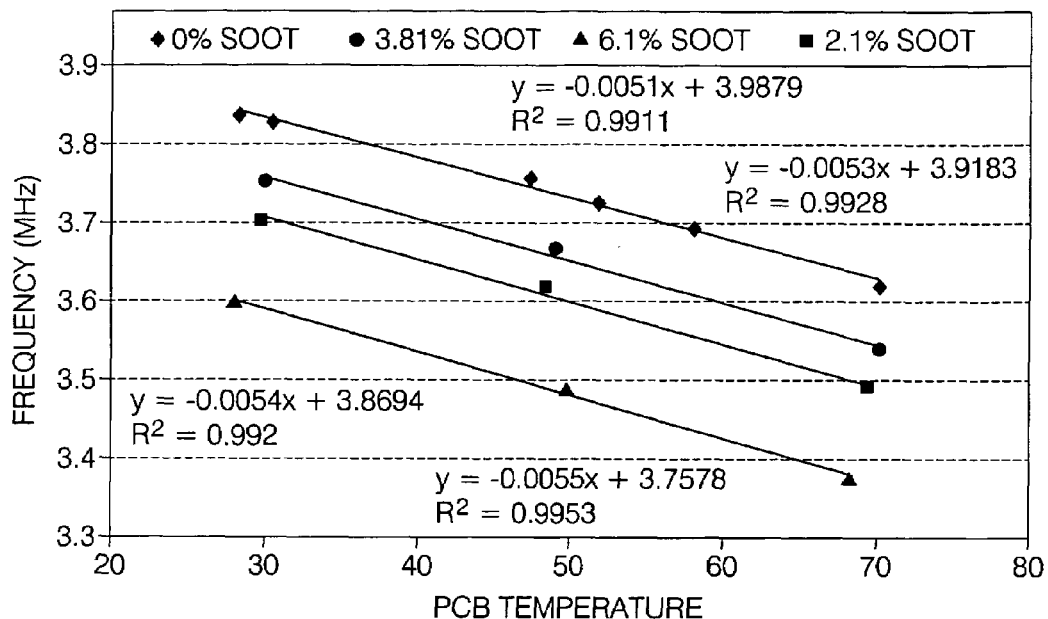
FIG. 6 is a graph showing the measured, uncompensated frequency versus PCB temperature for various levels of oil soot content.
Figure 7:
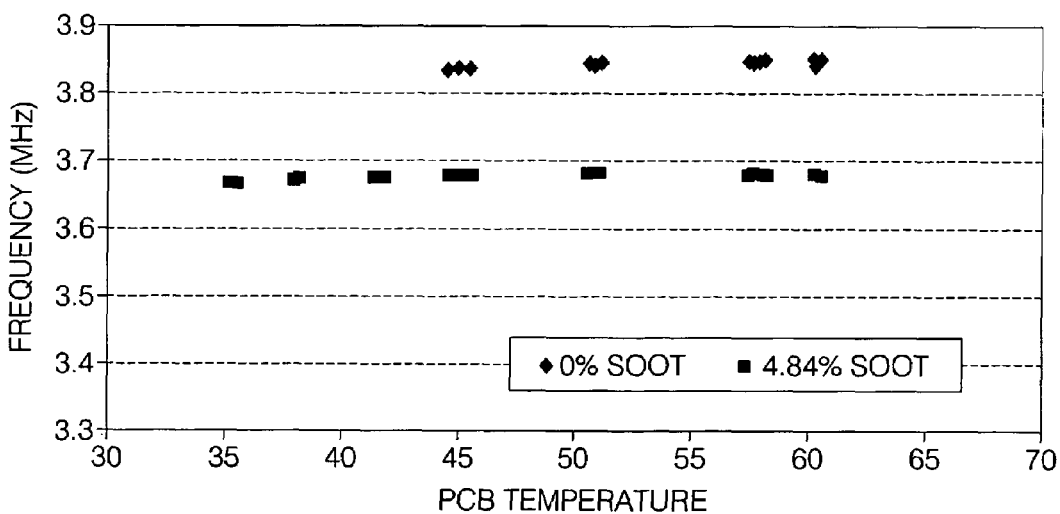
FIG. 7 is a graph showing the measured frequency compensated for PCB temperature versus PCB temperature at two different levels of oil soot content.

FIG. 6 is a graph showing the uncompensated frequency measured using the embodiment of the sensor 10 shown in FIG. 5. The measured, uncompensated frequency (in MegaHertz) is shown as a function of PCB temperature for various levels of soot content in oil 28. FIG. 6 also shows the linear functions associated with respective sloped lines drawn using measured points in oil with 0%, 2.1%, 3.81% and 6.1% soot content. FIG. 7 is a graph showing the measured frequency compensated for PCB temperature at 4.84% soot and at 0% soot.

Figure 8:
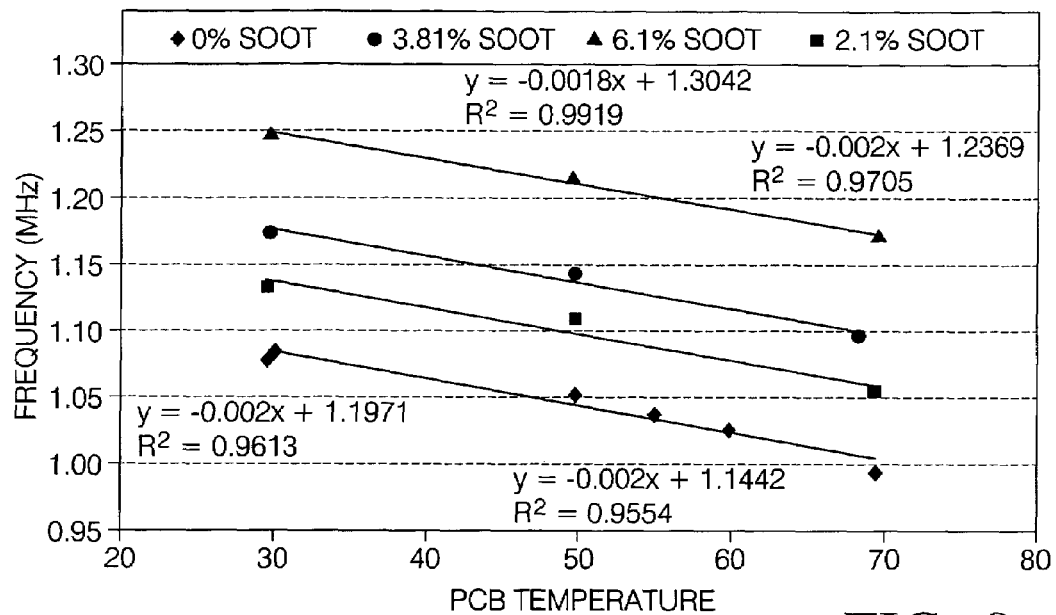
FIG. 8 is a graph showing measured, uncompensated loop current versus oil temperature for the same levels of oil soot content as shown in FIG. 6.
Figure 9:
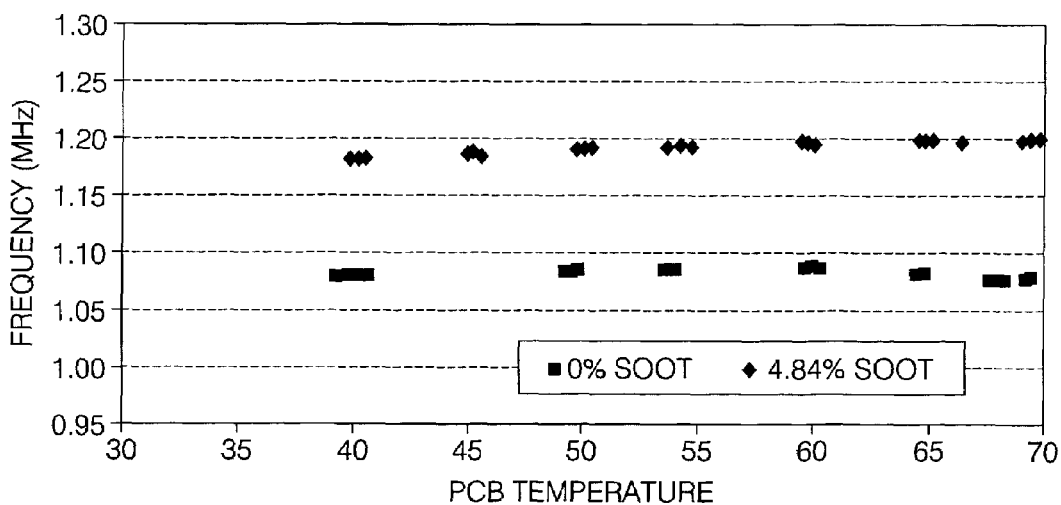
FIG. 9 is a graph showing the measured loop current compensated for temperature versus oil temperature at the same two levels of oil soot content as shown in FIG. 7.

FIG. 8 is a graph showing, for the same oil soot content as used in FIG. 6, the uncompensated loop current measured by the same sensor 10 versus oil temperature. The loop current is shown on the graph as the voltage $\hat{V}_{lpf}$. It should also be noted that in these measurements the PCB temperature is at the same temperature as the oil. As with respect to FIG. 6, FIG. 8 also shows the linear functions associated with respective sloped lines drawn using measured points in oil with 0%, 2.1%, 3.81% and 6.1% soot. The measured loop current compensated for temperature $V_{lpf}$ is shown versus oil temperature in FIG. 9 at 4.84% soot and at 0% soot. In this case, the oil and PCB temperatures are different. Specifically, the PCB temperature was in the range from 37° C. to 70° C. for the same sensor.

Figure 10:
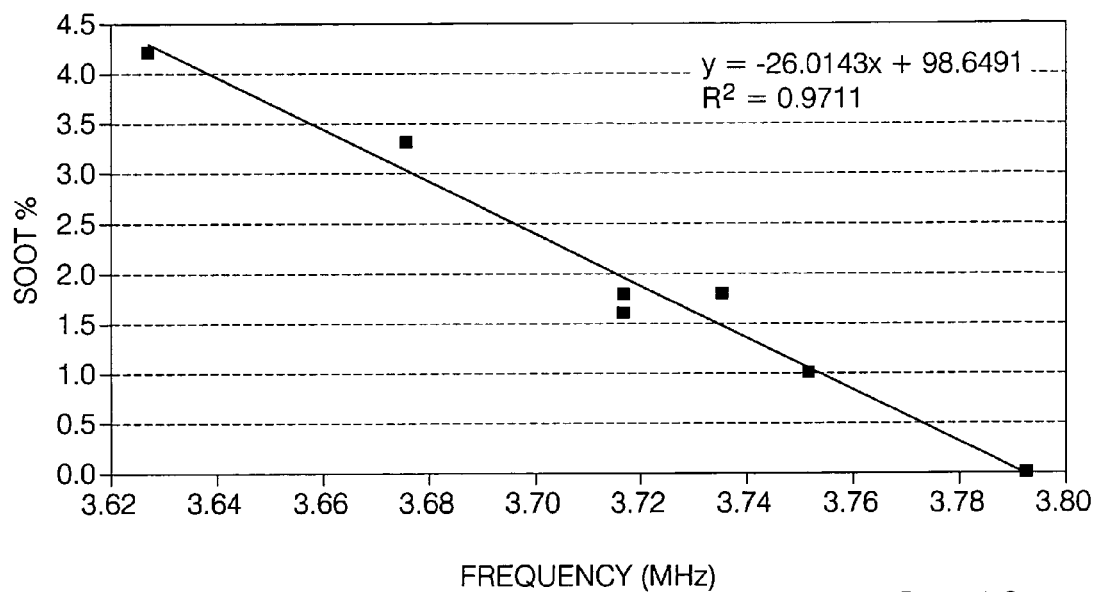
FIG. 10 is a graph showing the resonant frequency versus soot concentration an embodiment of the sensor according to FIG. 5.
Figure 11:
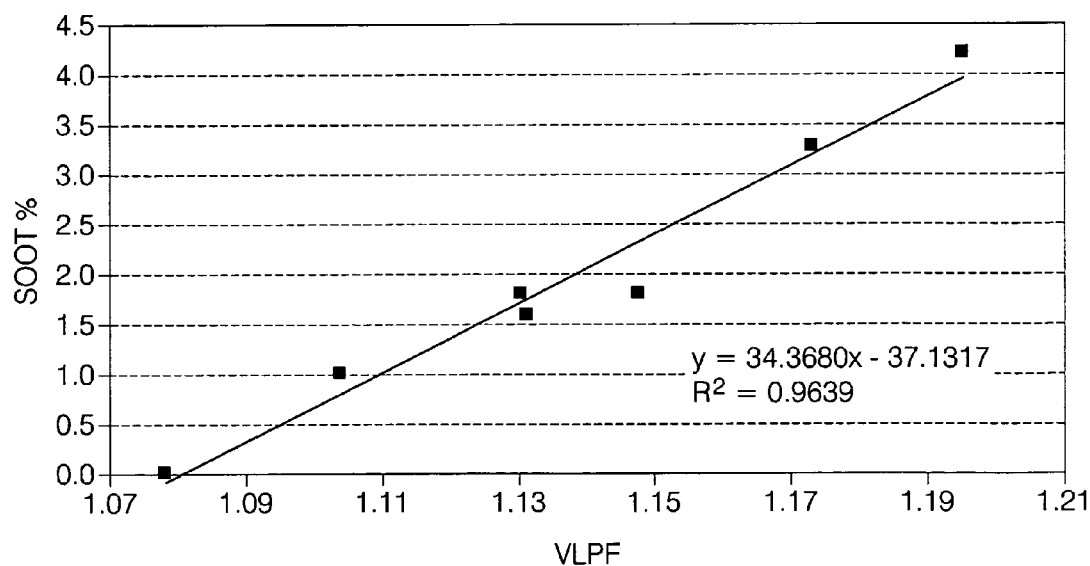
FIG. 11 is a graph showing the loop current versus soot concentration for the sensor used in obtaining FIG. 10.

After compensating for temperature, the results of the testing show that the resonant frequency decreases with increasing soot levels, and the loop current increases with increasing soot concentration. FIG. 10 shows the resonant frequency versus soot concentration another embodiment of the sensor 10 according to FIG. 5, and FIG. 11 shows the loop current versus soot concentration for the same sensor 10. Each of FIGS. 10 and 11 includes an equation that governs the relationship of the respective variables determined from the measured output values.

Figure 12:
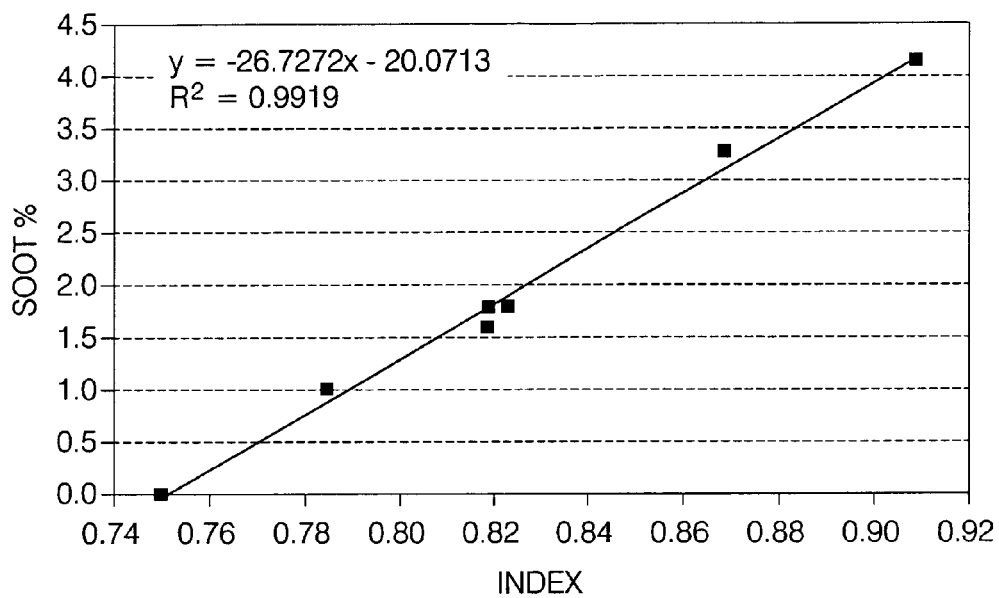
FIG. 12 is a graph of the sensor output index versus the percentage of soot in oil for the sensor used in obtaining FIG. 10.

A sensor output index is defined as:

$$\text{Index} = \frac{10 V_{lpf}}{f^2};$$

where $V_{lpf}$ the compensated current output (i.e., the resonant loop current) of the sensor; and f is the measured, compensated resonant frequency. A graph of the sensor output index versus soot concentration (the percentage of soot in oil) is shown in FIG. 12. As can be seen, this relationship is also a linear one. With the sensor output index, soot content can be calculated according to yet another variation of the invention. Specifically, during a calibration process a plurality of samples with known soot content can be tested using the disclosed sensor 10. The microcontroller 60, 98 can then calculate the Index values corresponding to each of the known soot concentrations and create a formula associated with the linear relationship of the Index value to a soot concentration such as that shown in FIG. 12. Then, when testing oil with an unknown soot percentage, the calculated Index can be used in the formula to determine the soot percentage of the tested oil.

Figure 13:
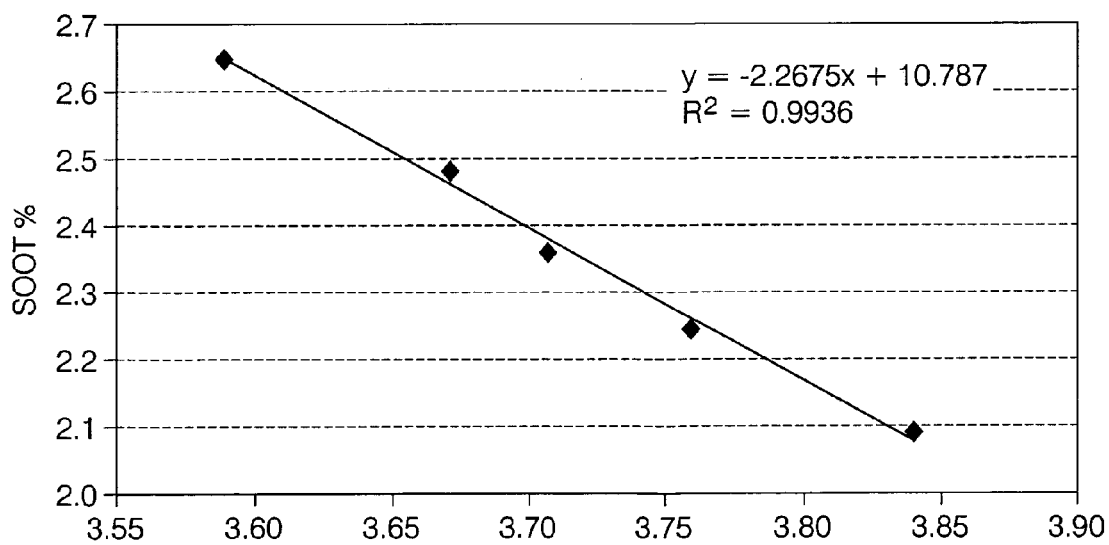
FIG. 13 is a graph showing the calibration of a sensor's resonant frequency versus the oil dielectric constant.

An added benefit to the invention exists in that the compensated resonant frequency can be used to calculate the permittivity or dielectric constant of the oil. This is another variable that can be an indicator of the oil's condition, even if it is typically considered less important that soot concentration. FIG. 13 is a graph showing the calibration of a sensor's resonant frequency versus the oil dielectric constant. Again, a linear relationship is shown. Similar to the description of the use of the Index to determine soot content in practice, the temperature-compensated resonant frequency can be used to determine the dielectric constant. More specifically, during a calibration process a plurality of samples with known dielectric constants can be tested using the disclosed sensor 10. The microcontroller 60, 98 can then calculate the temperature-compensated frequency corresponding to each of the known dielectric constants and create a formula associated with the linear relationship of the frequency to a dielectric constant such as that shown in FIG. 13. Then, when testing oil with an unknown dielectric constant, the measured, temperature-compensated resonant frequency can be used in the formula to determine the dielectric constant of the tested oil.

The previous discussion shows that the temperature dependencies are reproducible and can be calibrated out of the results. Some assumptions were made in coming to these conclusions. First, under normal operating conditions, the oil temperature is greater or equal to the PCB temperature, so the assumption of $T_{oil}$. $T_{pcb}$ was made. In addition, the sensor 10 was calibrated using oil temperatures between 30° C. and about 70° C. As mentioned, in this oil temperature range the loop current has an approximately linear relationship with the oil temperature and with the temperature difference between the oil and the PCB temperatures. Although the invention is not limited to operation in this temperature range, additional calibration may be necessary if operating outside this range.

Figure 14:
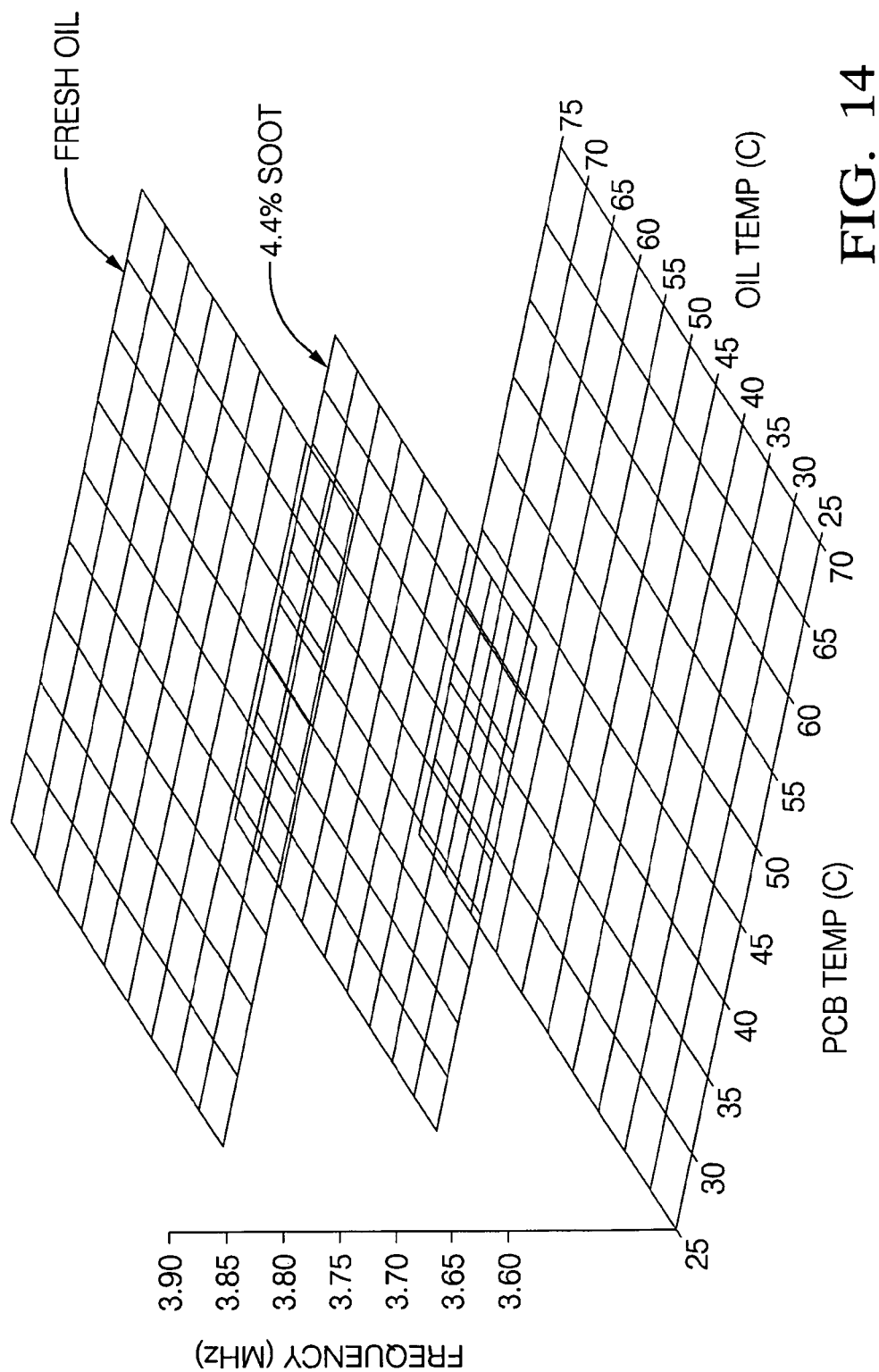
FIG. 14 is a three-dimensional plot of the sensor output resonant frequency as a function of both oil and PCB temperatures when the sensor is immersed in fresh oil and then the same oil with 4.4% soot.
Figure 15:
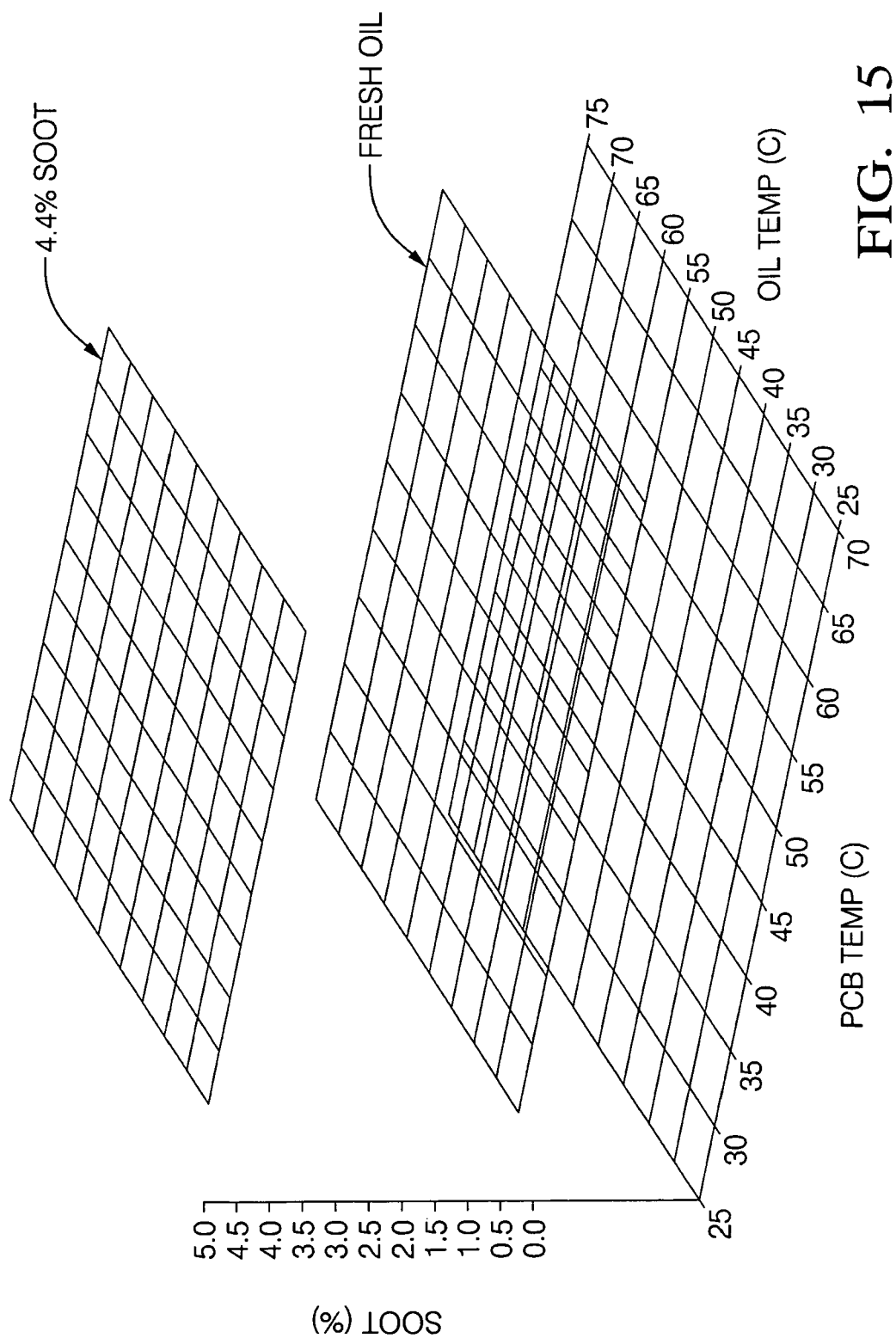
FIG. 15 is a three-dimensional plot of the sensor's soot output as a function of oil and PCB temperatures in the same two oils.

In order to test the temperature compensation in the method disclosed herein, tests of a prototype sensor were performed in a test engine with different oils having differing soot concentrations of up to 8%. The three-dimensional plot of FIG. 14 shows the sensor output resonant frequency as a function of both oil and PCB temperatures wherein the sensor is immersed in fresh oil and then the same oil with 4.4% soot. FIG. 15 similarly shows the sensor output soot as a function of oil and PCB temperatures in the same two oils. The data was collected at oil temperatures between 30° to 70° C. and PCB temperatures below the respective oil temperatures. The maximum variation of the resonant frequency measurement in this test was less than 0.032 MHz. The maximum variation of soot measurement in this test was less that 0.5%.

Figure 16:
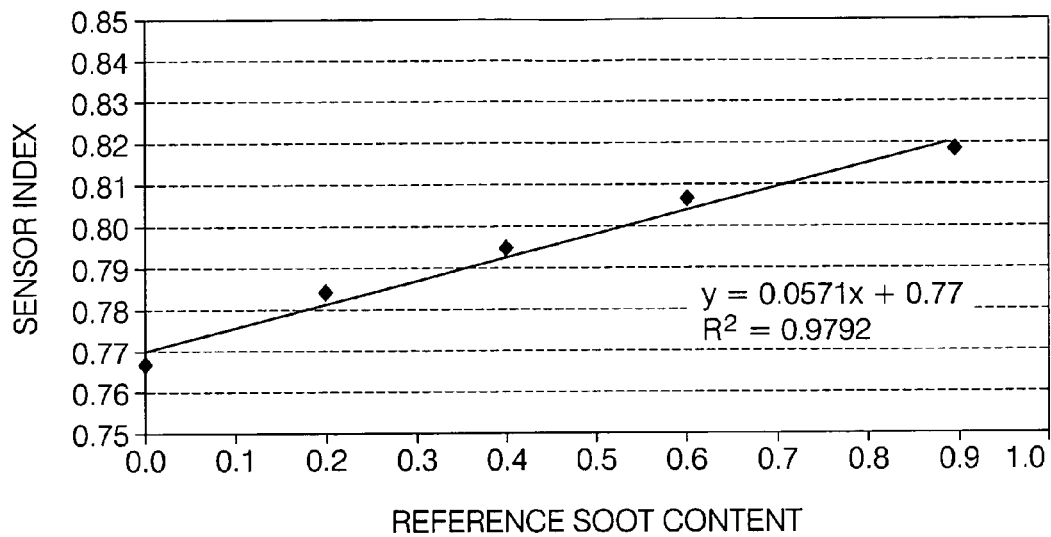
FIG. 16 is a graph showing the calculated sensor soot index plotted as a function of soot content measured using one common optical method.
Figure 17:
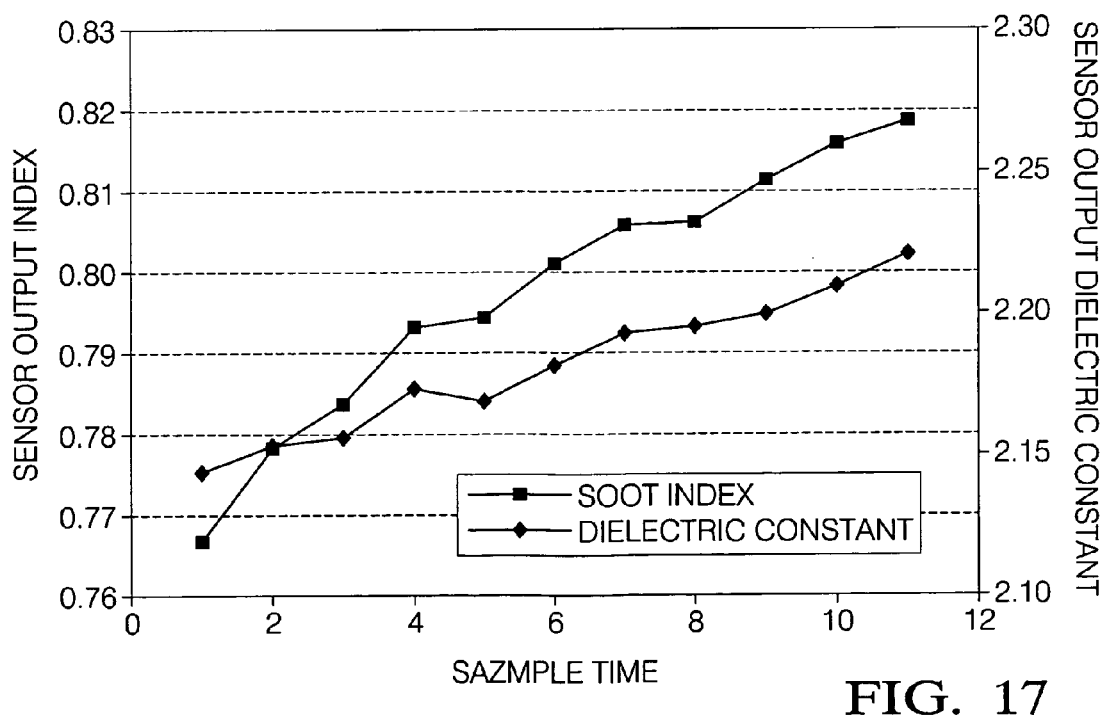
FIG. 17 is a graph showing the sensor index of FIG. 16 and dielectric constant output measured at various engine running times.

Comparisons of the sensor output using oil having known soot concentrations and to other methods of measuring soot concentration were performed. FIG. 16 is a graph showing the calculated sensor soot index as described above plotted as a function of soot content (in %) measured using one common optical method. A roughly linear relationship can be shown. FIG. 17 is a graph showing the same sensor index and dielectric constant output measured at various engine running times.

Figure 18:
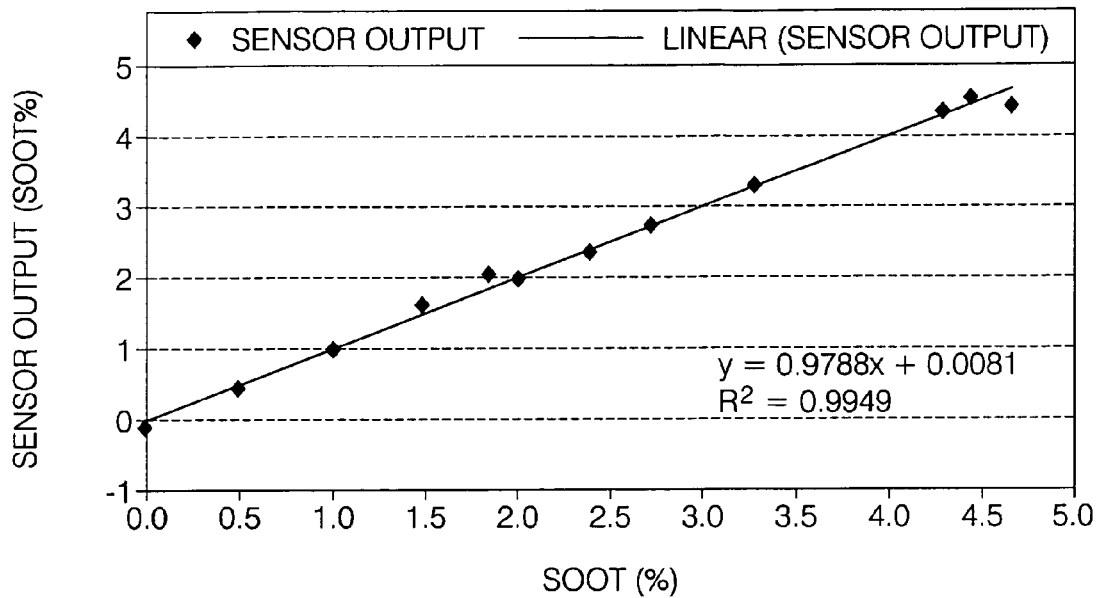
FIG. 18 is a graph showing the soot level indicated by a prototype sensor when immersed in test oils with soot levels up to 5%.
Figure 19:
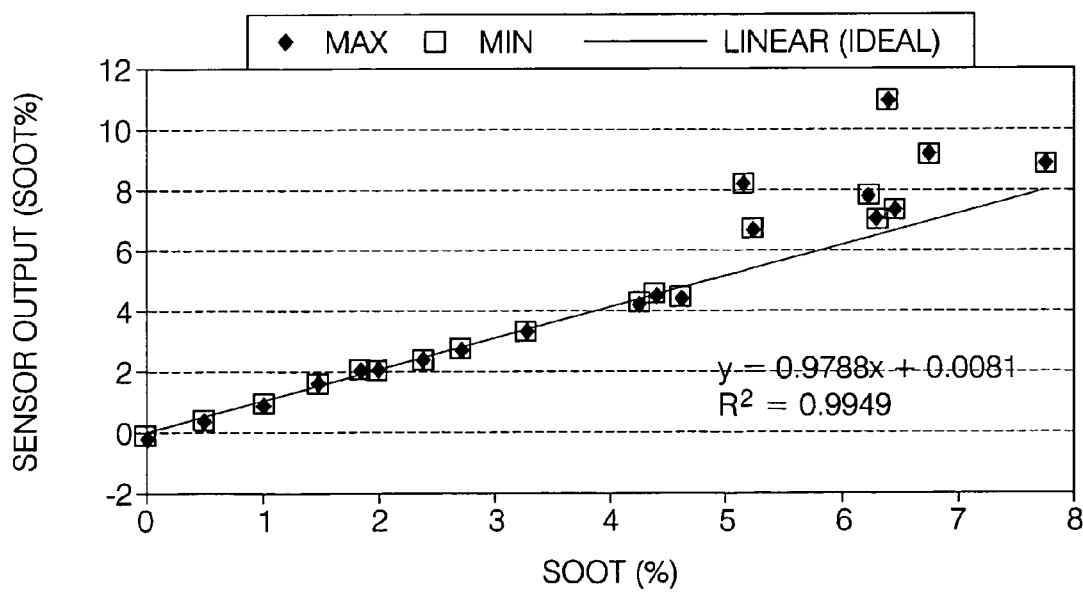
FIG. 19 is a graph showing the soot level indicated by the sensor used in generating FIG. 18 when immersed in test oils with soot levels up to about 8%.

The final two graphs shown in FIGS. 18 and 19 show the soot level output by the prototype sensor. FIG. 18 shows the soot level indicated by the sensor when immersed in test oils with soot levels up to 5%. FIG. 19 shows the output of the same sensor when immersed in test oils with soot levels up to 7.8%. The data was taken when the oil temperature reached 60° C., with a PCB temperature of around 50° C. For each oil sample, five measurements were performed under the same conditions. FIG. 19 shows both the highest reading and the lowest reading out of the five measurements. One can see that the highest and lowest readings are almost on top of each other. This means that the sensor repeatability is very good.

The Table below summarizes the test oils used in generating the data of FIGS. 18 and 19 and compares the measured values using the invention against a known reference soot content and values measured by an infrared soot meter.

for high soot level oils are not completely clear. Without being bound by theory, it is believed that with a high soot concentration present in the oil, the dispersant additives are overwhelmed such that the oil becomes non-uniform. The soot particles apparently attract each other to form long chains or relative big-size balls. Thus, the assumptions underlying the theory of measurement may no longer hold. Fortunately, at such soot levels the oil should be changed in any case. Also, it was found and can be seen in the Table that the sensor soot output is higher than the soot content measured optically for all oil tested. This may indicate that the optical measurements are saturated and underestimate the real soot content. Repeated thermogravimetric analysis (TGA) measurements on oils with soot contents above 5% show a large number of values are irreproducible. In any event, the high sensor output at worst will give a false positive alarm, indicating engine oil is bad when it is not, and will not result in an indication that oil is good when it is bad.

During normal operation of the sensor, the microcontroller 60, 98 measures the oil temperature first. If the oil temperature is in the predefined temperature range, in the illustrated embodiments between 30° and 70°, then the sensor 10 is ready to do the soot measurement. The excitation frequency is measured, as is the resonating loop current. Then, the PCB temperature is measured. The frequency and current are temperature-compensated and the soot content and, optionally, the dielectric constant are then calculated. Using the embodiment of FIG. 5 to illustrate, soot measurement using the microcontroller 98 includes the following steps:

| Oil Brand/Grade | Eng. Hrs. | Oil Hrs. | Eng. Miles | Oil Miles | Reference soot content | Infrared Soot Meter | Sensor soot content |
|---|---|---|---|---|---|---|---|
| Texaco ® Ursa 15w40 | 0 | 0 | 0 | 0 | — | 0 | −0.1 |
| Chevron ® H 15w40 | — | — | 83850 | 14726 | 0.56 | 0.56 | 0.4 |
| Premium E 15w40 | 279.35 | 16.1 | — | — | 0.99 | 0.99 | 1.0 |
| Premium Blue 15w40 | 302.6 | 39.4 | — | — | 1.48 | 1.48 | 1.5 |
| — | — | — | — | — | 1.84 | 1.84 | 2.0 |
| PC-9 | 35.1 | 35.1 | — | — | 1.99 | 1.99 | 2.0 |
| PC-9 | 921.5 | 37.8 | — | — | 2.4 | 2.4 | 2.3 |
| Premium Blue 15w40 | 192.5 | 192.5 | — | — | 2.73 | 2.73 | 2.7 |
| 15w40 (no brand) | 4346.1 | 22.7 | — | — | 3.63 | 3.3 | 3.2 |
| — | — | — | 418338 | — | 4.52 | 4.3 | 4.3 |
| PC-9 | 82.6 | 82.6 | — | — | 4.49 | 4.45 | 4.5 |
| — | — | — | 146715 | 35467 | 4.66 | 4.66 | 4.4 |
| — | — | 125 | — | — | 5.2 | 5.2 | 8.1 |
| PC-9 | 1001.6 | 117.9 | — | — | 5.03 | 5.3 | 6.7 |
| Premium Blue 15w40 | — | 165 | — | — | 6.26 | 6.3 | 7.7 |
| 15w40 (no brand) | 4303.1 | 84.7 | — | — | 6.38 | 6.38 | 7.0 |
| — | — | — | — | — | 6.46 | 6.46 | 10.8 |
| 15w40 (no brand) | 4286 | 67.6 | — | — | 6.53 | 6.53 | 7.3 |
| Shell ® Rimula Super | — | 2419.3 | 36094 | — | 6.83 | 6.83 | 9.0 |
| Shell ® Rimula Super | — | 1939 | — | 29039 | 7.8 | 7.8 | 8.7 |

From FIGS. 18 and 19, it can be concluded that the sensor output is accurate to within about ±0.2% at soot levels below 5%. Of course, this is the operating range of most Diesel engines. We can also conclude that the sensor outputs are high and have a wide scatter of about 2% to 3% at soot levels above 5%. So far, the root causes of the sensor output scatter 1. Measure the oil temperature using temperature sensor 106;
2. After the oil temperature reaches a value within the predefined temperature range, enable the PLL IC 82;
3. Wait for the analog circuit to reach a steady-state condition (around 5 seconds);
4. Measure the VCO input voltage (98*d*) to determine the excitation frequency;
5. Measure the resonating loop current (98*a*);
6. Disable the PLL IC 82;
7. Measure the PCB temperature using temperature sensor 108;
8. Calculate temperature-compensated frequency and loop current using the formulas described herein;
9. Calculate soot content and, optionally, the dielectric constant.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A method for determining characteristics of Diesel engine lubrication oil, comprising the steps of:
    immersing a capacitor in the oil such that the oil provides a dielectric between the plates thereof;
    connecting an inductor in series with the capacitor, wherein the capacitor and the inductor collectively provide a resonance circuit;
    varying a frequency of a high frequency voltage applied to the resonance circuit;
    sensing a temperature of the inductor;
    sensing when the resonance circuit is at resonance to thereby obtain at least one of a resonant frequency and a resonant current;
    compensating at least one of the resonant frequency and the resonant current for the temperature of the inductor; and
    using at least one of the compensated resonant frequency and the compensated resonant current to determine at least one of a soot content and a dielectric constant of the oil.

2. The method according to claim 1 wherein the step of sensing when the resonance circuit is at resonance further comprises the steps of:
    sensing a current value for each of a plurality of frequencies of the high frequency voltage applied to the resonance circuit during the varying step; and
    detecting a maximum value of the current wherein the maximum value of the current represents the resonant current.

3. The method according to claim 2 wherein the step of sensing when the resonance circuit is at resonance further comprises the step of:
    sensing an input voltage to a drive device varying the frequency of the high frequency voltage applied to the resonance circuit for the same plurality of frequencies of the high frequency voltage applied to the resonance circuit during the varying step; and wherein the input voltage when the maximum value of the current is detected represents the resonant frequency.

4. The method according to claim 3, further comprising the step of:
    calibrating measurements of at least one of the resonant current and the resonant frequency taken when the step of sensing when the resonance circuit is at resonance detects that the resonance circuit is at resonance, the calibrating step occurring while the temperature of the inductor is at a reference temperature.

5. The method according to claim 3, further comprising the step of:
    compensating the resonant frequency for the temperature of the inductor using the formula $f_c = m_f(T_{ref} - T_{pcb}) + f_m$; wherein $f_c$ is the compensated resonant frequency, $f_m$ is the resonant frequency, $m_f$ is a slope of frequency with respect to inductor temperature, $T_{ref}$ is a reference temperature, and $T_{pcb}$ is the temperature of the inductor; and wherein the step of using at least one of the compensated resonant frequency and the compensated resonant current to determine at least one of the soot content and the dielectric constant of the oil further comprises the step of using the compensated resonant frequency to determine the dielectric constant of the oil.

6. The method according to claim 3, further comprising the step of:
    sensing a temperature of the oil.

7. The method according to claim 6, further comprising the steps of:
    calibrating measurements of at least one of the resonant current and the resonant frequency taken when the step of sensing when the resonance circuit is at resonance detects that the resonance circuit is at resonance, the calibrating step occurring while the temperature of the inductor is at a reference temperature; and
    calibrating measurements of at least one of the resonant current and the resonant frequency taken when the step of sensing when the resonance circuit is at resonance detects that the resonance circuit is at resonance, the calibrating step occurring while the temperature of the oil is at the reference temperature.

8. The method according to claim 6, further comprising the step of:
    delaying the step of sensing when the resonance circuit is at resonance until the temperature of the oil is within a predetermined temperature range.

9. The method according to claim 6, further comprising the steps of:
    compensating the resonant frequency for the temperature of the inductor using the formula $f_c = m_f(T_{ref} - T_{pcb}) + f_m$ wherein $f_c$ is the compensated resonant frequency, $f_m$ is the resonant frequency, $m_f$ is a slope of frequency with respect to inductor temperature, $T_{ref}$ is a reference temperature, and $T_{pcb}$ is the temperature of the inductor; and
    compensating the resonant current for the temperature of the inductor and the temperature of the oil using the formulas $V_c = m_c(T_{ref} - T_{oil}) + V_m$ and $m_c = \alpha(T_{oil} - T_{pcb}) + m_{uc}$ wherein $V_c$ is the compensated resonant current, $V_m$ is the resonant current; $m_c$ is a slope of loop current with respect to oil temperature compensated for temperature; $m_{uc}$ is the slope of loop current with respect to oil temperature, $T_{ref}$ is the reference temperature, $T_{oil}$ is the temperature of the oil, $T_{pcb}$ is the temperature of the inductor, and $\alpha$ is an adjust factor.

10. The method according to claim 9 wherein the step of using the compensated resonant current and the compensated resonant frequency to determine the soot content of the oil further comprises the steps of:
  calculating a soot index according to the formula Index=10 $V_c/f_c^2$ wherein Index is the soot index, $V_c$ is the compensated resonant current and $f_c$ is the compensated resonant frequency; and
  comparing the soot index to a plurality of known soot index values associated with known soot content values.

11. The method according to claim 1 wherein the step of sensing when the resonance circuit is at resonance further comprises the steps of:
  sensing a difference of phase between current and voltage of the resonance circuit during the varying step;
  determining when the difference equals zero; and
  determining at least one of the resonant frequency and the resonant current when the difference equals zero.

12. The method according to claim 11 wherein the step of determining at least one of the resonant frequency and the resonant current further comprises the step of:
  determining a voltage of the resonance circuit when the difference equals zero; and wherein the voltage represents the resonant frequency.

13. The method according to claim 12 wherein the step of determining at least one of the resonant frequency and the resonant current further comprises the step of:
  determining a current of the resonance circuit when the difference equals zero; and wherein the current represents the resonant current.

14. The method according to claim 13, further comprising the step of:
  calibrating measurements of at least one of the resonant current and the resonant frequency taken when the step of sensing when the difference equals zero, the calibrating step occurring while the temperature of the inductor is at a reference temperature.

15. The method according to claim 13, further comprising the step of:
  compensating the resonant frequency for the temperature of the inductor using the formula $f_c=m_f(T_{ref}-T_{pcb})+f_m$; wherein $f_c$ is the compensated resonant frequency, $f_m$ is the resonant frequency, $m_f$ is a slope of frequency with respect to inductor temperature, $T_{ref}$ is a reference temperature, and $T_{pcb}$ is the temperature of the inductor; and wherein the step of using at least one of the compensated resonant frequency and the compensated resonant current to determine at least one of the soot content and the dielectric constant of the oil further comprises the step of using the compensated resonant frequency to determine the dielectric constant of the oil.

16. The method according to claim 13, further comprising the step of:
  sensing a temperature of the oil.

17. The method according to claim 16, further comprising the steps of:
  calibrating measurements of at least one of the resonant current and the resonant frequency taken when the difference is zero, the calibrating step occurring while the temperature of the inductor is at a reference temperature; and
  calibrating measurements of at least one of the resonant current and the resonant frequency taken when the difference is zero, the calibrating step occurring while the temperature of the oil is at the reference temperature.

18. The method according to claim 16, further comprising the steps of:
  compensating the resonant frequency for the temperature of the inductor using the formula $f_c=m_f(T_{ref}-T_{pcb})+f_m$ wherein $f_c$ is the compensated resonant frequency, $f_m$ is the resonant frequency, $m_f$ is a slope of frequency with respect to inductor temperature, $T_{ref}$ is a reference temperature, and $T_{pcb}$ is the temperature of the inductor; and
  compensating the resonant current for the temperature of the inductor and the temperature of the oil using the formulas $V_c=m_c(T_{ref}-T_{oil})+V_m$ and $m_c=\alpha(T_{oil}-T_{pcb})+m_{uc}$ wherein $V_c$ is the compensated resonant current, $V_m$ is the resonant current; $m_c$ is a slope of loop current with respect to oil temperature compensated for temperature; $m_{uc}$ is the slope of loop current with respect to oil temperature, $T_{ref}$ is the reference temperature, $T_{oil}$ is the temperature of the oil, $T_{pcb}$ is the temperature of the inductor, and $\alpha$ is an adjust factor.

19. The method according to claim 18, wherein the step of using the compensated resonant current and the compensated resonant frequency to determine the soot content of the oil further comprises the steps of: calculating a soot index according to the formula Index=10 $V_c/f_c^2$ wherein Index is the soot index, $V_c$ is the compensated resonant current and $f_c$ is the compensated resonant frequency; and comparing the soot index to a plurality of known soot index values associated with known soot content values.

20. The method according to claim 1, further comprising the step of:
  sensing a temperature of the oil.

21. The method according to claim 20, further comprising the step of:
  delaying the step of sensing when the resonance circuit is at resonance until the temperature of the oil is within a predetermined temperature range.

22. The method according to claim 20, further comprising the steps of:
  compensating a resonant frequency measured when the resonance circuit is at resonance for the temperature of the inductor to obtain the compensated resonant frequency; and
  further compensating the resonant current for the temperature of the oil.

23. The method according to claim 22 wherein the step of using at least one of the resonant frequency and the resonant current to determine at least one of a soot content and a dielectric constant of the oil further comprises the step of using the compensated resonant frequency to determine the dielectric constant of the oil.

24. The method according to claim 1, further comprising the step of:
  calibrating measurements of at least one of the resonant current and the resonant frequency taken when the step of sensing when the resonance circuit is at resonance detects that the resonance circuit is at resonance, the calibrating step occurring while the temperature of the inductor is at a reference temperature.

25. The method according to claim 24, further comprising the steps of:
  sensing a temperature of the oil; and
  calibrating measurements of at least one of the resonant current and the resonant frequency taken when the step of sensing when the resonance circuit is at resonance detects that the resonance circuit is at resonance, the calibrating step occurring while the temperature of the oil is at the reference temperature.

* * * * *